Nov. 12, 1963 E. S. BOERNER Plant Pat. 2,299
ROSE PLANT
Filed Oct. 1, 1962
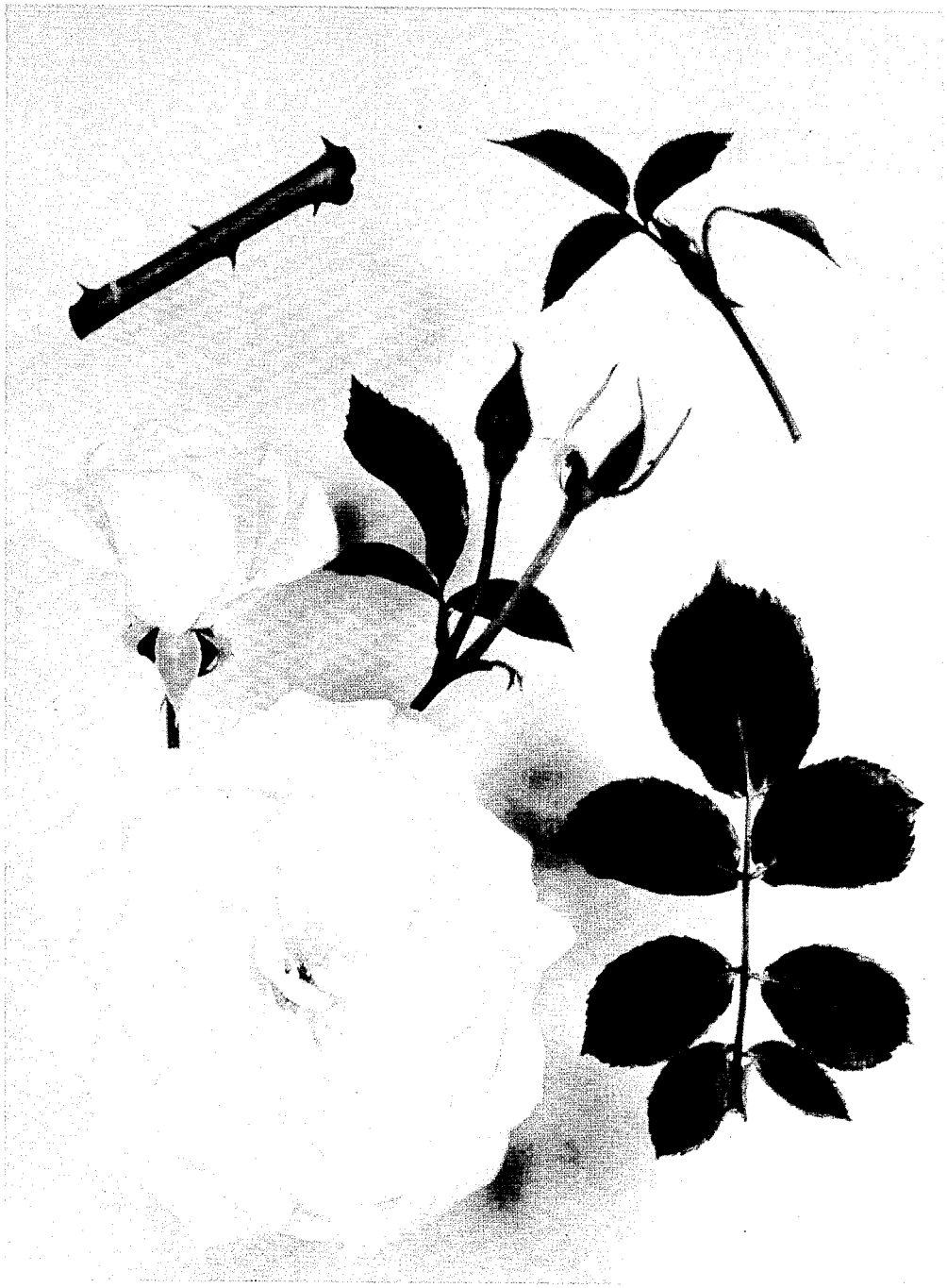
Inventor.
E. S. Boerner
By: Robb & Robb
Attorneys.

United States Patent Office

Plant Pat. 2,299

Patented Nov. 12, 1963

2,299

ROSE PLANT

Eugene S. Boerner, Newark, N.Y., assignor to Jackson & Perkins Company, Newark, N.Y., a corporation of New York Filed Oct. 1, 1962, Ser. No. 227,618
1 Claim. (Cl. Plt.—23)

The present invention relates to a new and distinct variety of Rose plant of the floribunda class, which was originated by me by crossing the variety known as "White Bouquet" (Plant Patent No. 1,415) with the variety known as "Princess White" (Plant Patent No. 1,540).

The primary objective of this breeding was to produce a new rose variety of the floribunda class which bears white flowers having stiffer petals that are capable of better resisting rain and wind when grown outdoors, as compared with former white floribunda roses. This objective was fully achieved, along with other desirable improvements, as evidenced by the following unique combination of characteristics which are outstanding in the new variety and which distinguish it from its parents, as well as from all other varieties of which I am aware:

(1) Stiff flower petals;

(2) Good resistance of the flowers to wind and rain when grown outdoors;

(3) An open flower form which is retained to the end; and (4) A distinctive and attractive white general color tonality of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"White Bouquet."
*Pollen parent.*—"Princess White."

Classification:
*Botanic.*—Floribunda.
*Commercial.*—Floribunda.

*Flower*

(Observations made from specimens grown outdoors at Newark, New York, near mid-morning during the middle of the month of August.)

Blooming Habit: Recurrent—continuous.

Bud:
*Size.*—Medium.
*Form.*—Ovoid; is not affected by wet or hot weather.
*Color.*—When sepals first divide—Marguerite Yellow, Plate 30. When petals begin to unfurl—White, Plate 53, lightly overcast with Marguerite Yellow, Plate 30. When half-blown: inside of petals—White, Plate 53, with lower half of petals very lightly overcast with Seafoam Yellow, Plate 31; reverse of petals—White, Plate 53.
*Sepals.*—Slightly branched; curl back when petals begin to unfurl. Color: inside—Pale Olivine, Plate 32; outside—Varley's Green, Plate 18, lightly overcast with Hay's Maroon, Plate 13.
*Calyx.*—Color—Varley's Green, Plate 18. Shape—pear. Size—small. Aspect—smooth. Odor when rubbed—none.
*Peduncle.* — Length — medium. Aspect — rough. Strength—erect; slender. Color—Rainette Green, Plate 31.
*Opening.*—Opens up well; is not affected by adverse weather conditions.

Bloom:
*Size.*—Medium. Average size when fully expanded—4 inches.
*Borne.*—Several together and in irregular clusters.
*Stems.*—Medium length; strong.
*Form (when first open).*—Open. Permanence—retains its form to the end.
*Petalage.*—Double (full but open center). Number of petals under normal conditions—from 30 to 35.
*Color.*—Center of flower—White, Plate 53, with lower half of petals very lightly overcast with Seafoam Yellow, Plate 31. Outer petals—White, Plate 53. Base of petals (aiglet)—Pale Chalcedony Yellow, Plate 17. Inside of petals—White, Plate 53. Reverse of petals—White, Plate 53. General tonality from a distance—White, Plate 53.
*Discoloration.*—General tonality at end of first day—White, Plate 53. Second day—White, Plate 53. Third day—White, Plate 53.

Petals:
*Texture.*—Thick; leathery; stiff; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Strong; very sweet. Nature—"Old Rose perfume."
*Lasting quality.*—On plant—very long. As cut flower—very long.

*Genital Organs*

Stamens, anthers: Small; many; regularly arranged around styles. Color—Cinnamon-Buff, Plate 29.
Stamens, filaments (threads): Medium length. Color—Light Chalcedony Yellow, Plate 17.
Pollen: Color—Pale Pinkish Buff, Plate 29.
Styles: Bunched; uneven length; short; thin.
Stigmas: Color—Pimrose Yellow, Plate 30.
Ovaries: All enclosed in calyx.
Hips: None.
Seeds: None.

*Plant*

Form: Bush.
Growth: Vigorous; upright; bushy.
Foliage: Compound of 5–7 leaflets.
*Size.*—Medium.
*Quantity.*—Abundant.
*Color.*—New foliage: upper side—Deep Dull Yellow-Green, Plate 32, with outer edges lightly overcast with Hay's Russet, Plate 14; under side—Dark Indian Red, Plate 27. Old foliage: upper side—Empire Green, Plate 32; under side—Jade Green, Plate 31.
*Shape.*—Oval pointed.
*Texture.*—Upper side—leathery. Under side—smooth.
*Ribs and veins.*—Ordinary.
*Edge.*—Serrated (saw-toothed).
*Serration.*—Both double and single; small.
*Leaf stem.*—Color—Van Dyke Red, Plate 13. Under side—prickly.

*Stipules.*—Medium length; bearded.

Wood:

*New wood.*—Color—Brownish-Olive, Plate 30. Bark—smooth.

*Old wood.*—Color—Bice Green, Plate 17. Bark—smooth.

Thorns:

*Thorns.*—Quantity: on main stalks from base—ordinary; on laterals from stalk—ordinary. Form—narrow base; medium length; hooked downward. Color (when young)—Madder Brown, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of stiff flower petals and good resistance of the flowers to wind and rain when grown outdoors, an open flower form which is retained to the end, and a distinctive and attractive white general color tonality of the flowers.

No references cited.